United States Patent
Lenz et al.

(10) Patent No.: US 12,357,440 B2
(45) Date of Patent: *Jul. 15, 2025

(54) CONTAINER FOR PRODUCING A DENTAL SYNTHETIC MATERIAL COMPOSITION

(71) Applicant: Ivoclar Vivadent AG, Schaan (LI)

(72) Inventors: Stephan Lenz, Feldkirch (AT); Benjamin Gebhardt, Grabs (CH); Theresa Sujata Maria Senti, Schaanwald (LI); Stefan Lerch, Bern (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

This patent is subject to a terminal disclaimer.

(21) Appl. No.: 18/498,682

(22) Filed: Oct. 31, 2023

(65) Prior Publication Data

US 2024/0058110 A1 Feb. 22, 2024

Related U.S. Application Data

(63) Continuation of application No. 16/930,530, filed on Jul. 16, 2020, now Pat. No. 11,833,005.

(30) Foreign Application Priority Data

Jul. 22, 2019 (EP) ..................................... 19187559

(51) Int. Cl.
| | | |
|---|---|---|
| *A61C 19/00* | (2006.01) | |
| *A61K 6/80* | (2020.01) | |
| *B29C 67/24* | (2006.01) | |
| *B65D 35/08* | (2006.01) | |
| *B65D 35/38* | (2006.01) | |
| *B65D 81/32* | (2006.01) | |
| *B29L 23/00* | (2006.01) | |

(52) U.S. Cl.
CPC .............. *A61C 19/005* (2013.01); *A61K 6/80* (2020.01); *B65D 35/08* (2013.01); *B65D 35/38* (2013.01); *B65D 81/32* (2013.01); *B29C 67/246* (2013.01); *B29L 2023/00* (2013.01)

(58) Field of Classification Search
CPC ........ A61C 19/005; A61K 6/80; B65D 35/08; B65D 35/38; B65D 81/32; B29C 67/246; B29L 2023/00
See application file for complete search history.

(56) References Cited

U.S. PATENT DOCUMENTS

| | | |
|---|---|---|
| 2,939,610 A | 6/1960 | Castelli et al. |
| 2,944,705 A | 7/1960 | Strumor |
| 3,411,374 A | 11/1968 | Holly |
| 3,759,374 A | 9/1973 | Helger et al. |
| 4,804,115 A | 2/1989 | Ball |

(Continued)

FOREIGN PATENT DOCUMENTS

EP   3769943 A1   1/2021

*Primary Examiner* — Frederick C Nicolas
(74) *Attorney, Agent, or Firm* — Ann M. Knab; Thad McMurray

(57) ABSTRACT

A container (100) for producing a self-curing or dual-curing dental synthetic material composition (200), which container includes a deformable wall (101), having a first synthetic material component (103-1); and a second synthetic material component (103-2) for curing the synthetic material composition (200) or starting a curing reaction.

12 Claims, 3 Drawing Sheets

(56) References Cited

U.S. PATENT DOCUMENTS

| | | |
|---|---|---|
| 4,811,549 A | 3/1989 | Usami et al. |
| 5,215,215 A | 6/1993 | Sauer |
| 5,520,975 A | 5/1996 | Inoue et al. |
| 5,823,387 A | 10/1998 | Manadanas et al. |
| 6,126,923 A | 10/2000 | Burke et al. |
| 6,257,450 B1 | 7/2001 | Jackson et al. |
| 6,415,955 B1 | 7/2002 | Ostreicher |
| 6,454,130 B1 | 9/2002 | Miller et al. |
| 6,613,036 B1 | 9/2003 | Farmer et al. |
| 6,620,436 B1 | 9/2003 | Rolf |
| 7,337,925 B2 | 3/2008 | Imaizumi et al. |
| 7,617,950 B2 | 11/2009 | Norris et al. |
| 8,091,743 B2 | 1/2012 | Lester et al. |
| 8,946,138 B2 | 2/2015 | Kessler et al. |
| 9,512,388 B2 | 12/2016 | Meier et al. |
| 10,392,163 B2 | 8/2019 | May et al. |
| 11,391,614 B2 | 7/2022 | Senn |
| 11,833,005 B2 * | 12/2023 | Lenz ........................ A61K 6/80 |
| 2004/0137177 A1 | 7/2004 | Saito et al. |
| 2008/0029548 A1 | 2/2008 | De Wree et al. |
| 2011/0036875 A1 | 2/2011 | Radzwill |
| 2013/0123741 A1 | 5/2013 | Bolduc et al. |
| 2013/0310780 A1 | 11/2013 | Phillips |
| 2015/0265511 A1 | 9/2015 | Boyd et al. |
| 2016/0251606 A1 | 9/2016 | Peirsman et al. |
| 2017/0049668 A1 | 2/2017 | Fernandez et al. |
| 2017/0101253 A1 | 4/2017 | Faulhaber et al. |
| 2017/0156993 A1 | 6/2017 | Moszner et al. |
| 2019/0147535 A1 | 5/2019 | Hsieh |
| 2020/0030194 A1 | 1/2020 | Yoshinaga et al. |
| 2020/0046464 A1 | 2/2020 | Cinader, Jr. |
| 2021/0255016 A1 | 8/2021 | Senn |

* cited by examiner

CONTAINER FOR PRODUCING A DENTAL SYNTHETIC MATERIAL COMPOSITION

CROSS-REFERENCE TO RELATED APPLICATIONS

This application is a continuation application of and claims priority to U.S. patent application Ser. No. 16/930,530, filed Jul. 16, 2020, which claims priority to European patent application No. 19187559.0 filed on Jul. 22, 2019, the disclosures of which are incorporated herein by reference in their entirety.

TECHNICAL FIELD

The present invention relates to a container for producing a self-curing or dual-curing dental synthetic material composition and to a method for producing a self-curing or dual-curing dental synthetic or composite or plastic material composition. Dental synthetic material also includes but is not limited to dental resin, dental composite and dental polymeric materials.

BACKGROUND

In the field of dentistry, it is difficult to produce small amounts of dental synthetic material compositions which are mixed together from two different synthetic material components. For example, if the synthetic material components are removed manually from different tubes and are mixed together, it is difficult to maintain the correct mixing ratio. In addition, the homogeneity of the mixture should be ensured. Moreover, the sequence over time plays a role. If a user does not mix the synthetic material components quickly enough, the synthetic material composition is cured before the desired mixing quality is achieved. In addition, there is the risk of air being introduced into the mixture.

U.S. 20200093568, 20200046464, 20200030194, 20130123741, 20150265511, 20170101253, 20190147535, 2004137177, 6126923, 5520975, 5215214, and 4811549, are directed to compositions and/or containers for mixing compositions and are hereby incorporated by reference in their entirety.

SUMMARY

It is the technical object of the present invention to facilitate the production of a dental synthetic or polymeric material composition.

This object is achieved by the subject-matter of the independent claims. Advantageous embodiments are subject to the dependent claims, the description and the figures.

According to a first aspect, this object is achieved by a container for producing a self-curing or dual-curing dental synthetic material composition, which container comprises a deformable wall, having a first synthetic material component; and a second synthetic material component for curing the synthetic material composition or starting a curing reaction. The first synthetic material component and the second synthetic material component are disposed in an unmixed state in the container in different volume regions. The dental synthetic material composition can be used e.g. for treating a patient. The container can be a single-use container or a multi-use container. The container is deformable such that the two synthetic material components can be mixed by kneading the container.

In a kneading process, the deformable wall of the container is deformed so that a mechanical force can be exerted onto the two synthetic material components and these are mixed together. As a result, the dental synthetic material composition is produced within the container and can then be directly processed. The synthetic material composition is used e.g. for filling a tooth or gluing a crown. The container provides the technical advantage that the two synthetic material components can already be pre-metered in the container in the correct mixing ratio and even small amounts of the dental synthetic material composition can be produced simply and rapidly.

In a technically advantageous embodiment of the container, the container is the shape of a tube or bag. The bag can be prefabricated to be closed or can be made from one or two sheets and can temporarily become a closed container simply by being clipped. This provides e.g. the technical advantage that the synthetic material components can be rapidly and homogeneously mixed together.

In a further technically advantageous embodiment of the container, the deformable wall is formed from silicone. This provides e.g. the technical advantage that the container can be kneaded in a particularly effective manner in order to mix the two synthetic material components.

In a further technically advantageous embodiment of the container, the deformable wall is transparent in a wavelength range of 390 nm to 520 nm. This provides e.g. the technical advantage that the extent to which the synthetic material components have been mixed can be detected visually.

In a further technically advantageous embodiment of the container, the first synthetic material component and/or the second synthetic material component are disposed in a string-like manner within the container. This provides e.g. the technical advantage that the two synthetic material components can be homogeneously mixed over the length of the string by kneading.

In a further technically advantageous embodiment of the container, the container is provided on the inside or outside with a three-dimensional structure which supports the mixing of the material and/or prevents the synthetic material composition from oozing out during the mixing process.

In a further technically advantageous embodiment of the container, the container is configured such that it can be everted so that the outer surfaces are turned inwards and the inner surfaces are turned outwards. This provides e.g. the technical advantage that the metering of the synthetic material components and/or the removal of the mixed synthetic material composition are facilitated.

In a further technically advantageous embodiment of the container, the string-like first synthetic material component and the string-like second synthetic material component are twisted. This provides e.g. the technical advantage that the two synthetic material components can be mixed in an even better and simpler manner.

In a further technically advantageous embodiment of the container, the first synthetic material component comprises a polymerizable organic matrix having a mixture of monomers, initiator components, stabilisers and pigments.

In a further technically advantageous embodiment of the container, the first and/or second synthetic material components are in the form of a powder, paste or liquid.

In a further technically advantageous embodiment of the container, the synthetic material composition comprising the mixed first synthetic material component and second synthetic material component has a viscosity which is in the range of 50-3000 Pas for flowable synthetic material compositions and preferably between 3000-50000 Pas for stoppable synthetic material compositions. This provides e.g. the technical advantage that the produced synthetic material composition can be processed efficiently.

The viscosity of flowable and stoppable synthetic material components is measured using a rheometer in oscillating mode. Measuring is performed at room temperature (23.0° C.). Measuring is performed with a PP-MS (plate-plate measuring system). For stoppable synthetic material components, a plate diameter of 10 mm is used, and a plate diameter of 25 mm is used for flowable synthetic material components. Depending upon the filler composition, the gap distance is between 0.500 and 1.000 mm.

In a further technically advantageous embodiment of the container, the container comprises a spout for squeezing out the synthetic material composition. This provides e.g. the technical advantage that the produced synthetic material composition can be efficiently pressed out of the container and applied at the desired location.

According to a second aspect, this object is achieved by a method for producing a self-curing or dual-curing dental synthetic material composition, comprising the step of kneading a container having a deformable wall and including a first synthetic material component and a second synthetic material component for curing the synthetic material composition or starting a curing reaction. By means of the method, the same technical advantages are achieved as with the container according to the first aspect.

In an advantageous embodiment of the method, the container is heated to a predetermined temperature before or during the step of kneading. This provides e.g. the technical advantage that the mixing of the two synthetic material components is accelerated, e.g. by reducing the viscosity.

In an advantageous embodiment of the method, the kneading or mixing of the first and second synthetic material components is performed at low pressure or under vacuum. It may be the case that only the container is at low pressure or under vacuum, or the entire surroundings within the mixing chamber can be at low pressure or under vacuum.

BRIEF DESCRIPTION OF THE FIGURES

Exemplified embodiments of the invention are illustrated in the drawings and are described in more detail hereinunder.
In the figures.

DETAILED DESCRIPTION

Figure 1:
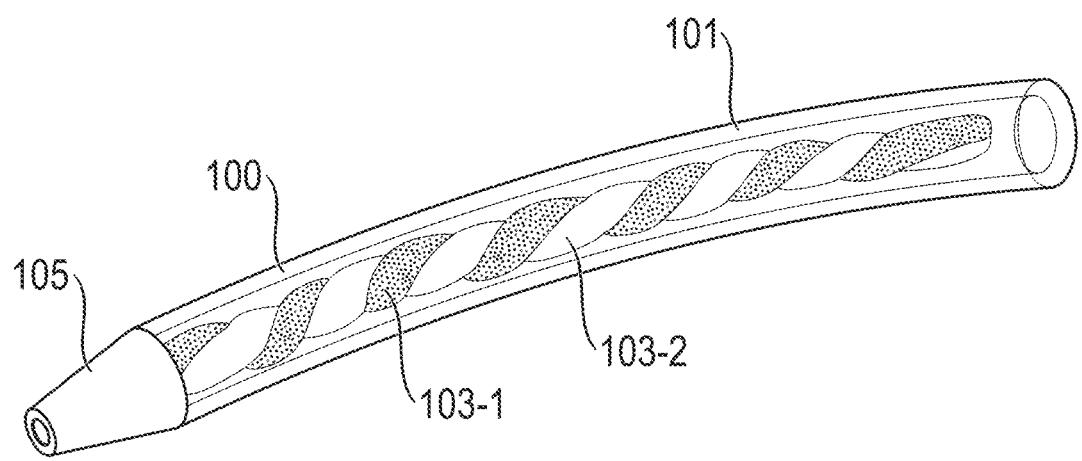
FIG. 1 shows a schematic illustration of a container for producing a self-curing or dual-curing dental synthetic material composition.

FIG. 1 shows a schematic illustration of a container 100 for producing a self-curing or dual-curing dental synthetic material composition. Within the container 100 in the shape of a tube, a weighed amount of a first synthetic material component 103-1 and a weighed amount of a second synthetic material component 103-2 are disposed.

In the case of a container 100 in the shape of a tube, a bag volume, i.e. length of the tube, can be easily adapted to the amount of material to be mixed. The container 100 in the shape of a tube has e.g. an outer diameter of 5 to 6 mm and a wall thickness of 1 mm. The volume of the container 100 is e.g. 1 ml.

The two synthetic material components 103-1 and 103-2 are disposed in an unmixed state in the container 100 in different volume regions. The two synthetic material components 103-1 and 103-2 are disposed in the container 100 in the shape of a tube which is then closed at one or both ends. The container 100 can be formed from a heat shrink tube which, when filled with the synthetic material components 103-1 and 103-2, has a large diameter and then becomes considerably smaller by way of heat. As a result, air in the container 100 can be displaced before the container is sealed and clipped at the ends. As a result, air bubbles cannot occur in the synthetic material composition 200. The container 100 can be used in a hand-held device or in a stationary device which kneads the container 100 and dispenses the synthetic material composition or the kneaded container with the synthetic material composition.

The wall 101 of the container 100 is elastically deformable so that a mechanical force can be exerted from the outside onto the two synthetic material components 103-1 and 103-2. For example, the deformable wall can be formed from an elastic silicone. Other examples of deformable materials include, but are not limited to, plastic film, non-woven fabric, or plastic textile. More specific examples include, but are not limited to, thermoplastic polyurethane (TPU), polyethylene, low-density polyethylene (LDPE), or linear low-density polyethylene (LLDPE)), nylon, silicone, rubber, polyethylene, polypropylene, polyvinylchloride, polyethylene tetraphalate (PET), similar thermoplastics or combinations of these.

The entire container 100 is kneaded to mix the two synthetic material components 103-1 and 103-2. As a result, the two synthetic material components 103-1 and 103-2 are mixed and a homogeneous synthetic material composition is produced within the container 100 which can then be processed. The synthetic material composition thus obtained is used e.g. for filling a tooth or for attaching a crown.

The synthetic material components 103-1 and 103-2 are present in a string-like manner and are intertwined in the form of a spiral. As a result, effective mixing of the two synthetic material components 103-1 and 103-2 can be achieved during the kneading process and a homogeneous synthetic material composition can be achieved. The two synthetic material components 103-1 and 103-2 can be powders, pastes, liquids or gels.

The first and/or second synthetic material components 103-1 and 103-2 may include e.g. one or more of a polymerizable organic matrix having a mixture of monomers, initiator components, stabilisers and pigments. Mixtures of dimethacrylates can be used as resins.

Materials which contain at least one multifunctional (meth)acrylate or a mixture of monofunctional and multifunctional (meth)acrylates as a radically polymerizable monomer (b) are preferred. The term "monofunctional (meth)acrylates" is understood to mean compounds with one radically polymerizable group and the term "multifunctional (meth)acrylates" is understood to mean compounds with two or more, preferably 2 to 4, radically polymerizable groups. The monofunctional or multifunctional (meth)acrylates can contain further functional groups, such as e.g. hydroxy, ester, silyl or ureido groups. Suitable monofunctional or multifunctional (meth)acrylates are 2-hydroxyethyl methacrylate, benzyl methacrylate, tetrahydrofurfuryl methacrylate or isobornyl methacrylate, p-cumyl-phenoxyethylene glycol methacrylate (CMP-1E), bisphenol-A-dimethacrylate, bis-GMA (an addition product of methacrylic acid and bisphenol-A-diglycidyl ether), ethoxylated or propoxylated bisphenol-A-dimethacrylate, such as e.g. 2-[4-(2-(meth)

acryloyloxy ethoxy ethoxy)phenyl]-2-[4-(2-methacryloyloxy ethoxy)phenyl]-propane) (Sr-348c, Sartomer; contains 3 ethoxy groups) or 2,2-bis[4-(2-methacryloxy propoxy)phenyl]propane (bis-PMA), UDMA (an addition product of 2-hydroxyethyl methacrylate and 2,2,4- or 2,4,4-trimethyl-hexamethylene-1,6-diisocyanate), di-, tri- or tetraethylene glycol dimethacrylate, trimethylolpropane trimethacrylate, pentaerythritol tetramethacrylate, as well as glycerin di- and trimethacrylate, bis-methacryloyloxymethyl-tricyclo[5.2.1.]decane (TCDMA), 1,4-butanediol dimethacrylate, 1,10-decanediol dimethacrylate (D3MA), 1,12-dodecandiol dimethacrylate, or mixtures thereof.

The following are particularly suitable: bisphenol-A-dimethacrylate, bis-GMA (an addition product of methacrylic acid and bisphenol-A-diglycidyl ether), 2-[4-(2-(meth)acryloyloxy ethoxy ethoxy)phenyl]-2-[4-(2-methacryloyloxy ethoxy)phenyl]-propane) (Sr-348c, Sartomer), 2,2-bis[4-(2-methacryloxy propoxy)phenyl]propane (bis-PMA), UDMA (an addition product of 2-hydroxyethyl methacrylate and 2,2,4- or 2,4,4-trimethyl-hexamethylene-1,6-diisocyanate), bis-methacryloyloxymethyl-tricyclo[5.2.1.]decane (TCDMA), and mixtures thereof.

The following can be used as additional fillers: inorganic particulate fillers, in particular oxides such as $SiO_2$, $ZrO_2$ and $TiO_2$ or mixed oxides comprising $SiO_2$, $ZrO_2$, $ZnO$ and/or $TiO_2$, nanoparticulate or micro-fine fillers, such as pyrogenic silica or precipitation silica, glass powder, such as quartz, glass ceramic or x-ray-opaque glass powder, preferably barium or strontium aluminium silicate glasses, and x-ray-opaque fillers, such as ytterbium trifluoride, tantalum (V) oxide, barium sulphate or mixed oxides of $SiO_2$ with ytterbium(III) oxide or tantalum(V) oxide.

Moreover, (isofillers) are suitable as prepolymers. These comprise a monomer mixture and filler components such as x-ray-opaque glass powder (barium or strontium aluminium silicate glasses), oxides such as $SiO_2$, $ZrO_2$ and $TiO_2$ and x-ray opaque filler (ytterbium trifluoride). This mixture is polymerized (thermal, light) and optionally post-processed (milling, sieving, silanising) to form fillers and added to the synthetic material mixture as a filler.

Initiators are added to the synthetic material components 103-1 and 103-2, by means of which the synthetic material components 103-1 and 103-2 can be polymerized in a self-curing or dual-curing manner. In the case of self-curing, the synthetic material composition is cured solely by the mixing of the two synthetic material components 103-1 and 103-2. The initiators listed below are distributed amongst the two synthetic material components 103-1 and 103-2 for self-curing polymerization performed at room temperature, in such a way that the individual synthetic material components 103-1 and 103-2 are stable and the polymerization reaction begins only when the two synthetic material components 103-1 and 103-2 contact one another. In the case of dual-curing, light can additionally be used to cure the synthetic material composition.

In the case of self-curing, the synthetic material composition is cured solely by the mixing of the two synthetic material components 103-1 and 103-2. In the case of dual-curing, light can additionally be used to cure the synthetic material composition.

Redox initiator combinations such as e.g. combinations of benzoyl peroxide with N,N-dimethyl-sym.-xylindine or N,N-dimethyl-p-toluidine are used as initiators for a self-curing polymerization performed at room temperature. Furthermore, redox systems comprising peroxides or hydroperoxides and such reduction agents, such as e.g. ascorbic acid, barbiturates, thioureas or sulfinic acids, are particularly suitable. The radical-forming speed of such redox initiator systems can be accelerated by catalytic amounts of transition metal compounds (metal redox catalysis). Compounds of transition metals which have at least 2-stable valency states can be used as transition metal redox catalysts. These are primarily compounds of the elements copper, iron, vanadium, nickel or cobalt, wherein copper compounds are particularly preferred, and these are preferably used as efficiently organosoluble compounds, such as e.g. acetylacetonate, naphthenate or 2-ethyl-hexanoate. Finally, ligands suitable for the transition metal compounds, or the complexes thereof, can also be added as further additives, in particular chelate ligands, such as e.g. 2-(2-aminoethyl-amino)ethanol, triethylene tetramine, dimethyl glyoxime, 8-hydroxyquinoline, 2,2'-bipyridine or 1,10-phenanthroline. In order to ensure sufficient storage stability, redox initiator system-based materials are mostly used as 2-component systems, wherein oxidation agents (peroxide or hydroperoxide) and reduction agents (amines, sulfinic acids, barbiturates, thioureas, etc.) are worked-in in separate components and are not mixed until shortly before application.

A combination of at least one monomolecular photoinitiator and at least one bimolecular photoinitiator, in particular those photoinitiators which are active in a wavelength range of 400 to 500 nm, are preferably used as light initiators for dual-curing. Preferably, the at least one monomolecular photoinitiator and the at least one bimolecular photoinitiator are used in a ratio of 2:1 to 1:2 based on their weight proportions.

Preferred monomolecular photoinitiators are mono- or bis-acyl phosphine oxides, diacyl dialkyl germanium and tetraacyl germanium compounds and tetraacyl stannanes. Particularly preferred monomolecular photoinitiators are 2,4,6-trimethylbenzoyl diphenylphosphine oxide, bis(2,4,6-trimethylbenzoyl)phenylphosphine oxide, dibenzoyl diethylgermane, bis(4-methoxybenzoyl)diethylgermane (MB-DEGe, Ivocerin®), tetrabenzoylgermane, tetrakis(o-methylbenzoyl)germane, tetrakis(mesitoyl)stannane and mixtures thereof.

α-diketones or derivatives thereof are preferably suitable as bimolecular photoinitiators. Particularly suitable α-diketones or derivatives thereof are camphorquinone (CQ), 9,10-phenanthrenequinone, 1-phenyl-propane-1,2-dione, 2,2-dimethoxy-2-phenyl-acetophenone, diacetyl or 4,4'-dichlorobenzil or derivatives thereof. Camphorquinone (CQ), 2,2-dimethoxy-2-phenyl-acetophenone and mixtures thereof are more particularly preferred. α-diketones in combination with amines are most preferred as reduction agents, such as e.g. 4-(dimethylamino)-benzoic acid ester (EDMAB), N,N-dimethylaminoethyl methacrylate, N,N-dimethyl-sym.-xylidine, triethanolamine and mixtures thereof. A ratio of bimolecular photoinitiator to amine of 1:1 to 1:6, based on their weight proportions, is preferably used.

The container 100 provides the technical advantage that the two synthetic material components 103-1 and 103-2 can already be pre-metered in the container 100 in the correct mixing ratio and also small amounts in the region of a few fractions of a gram of the dental synthetic material composition can be produced simply and rapidly. Since mixing of the two synthetic material components 103-1 and 103-2 occurs as required in the container 100, cleaning expenditure is obviated, and cross-contamination can be prevented. Adhesion or "excessive polymerization" of the synthetic material composition in a mixing mechanism can be prevented.

Figure 2:
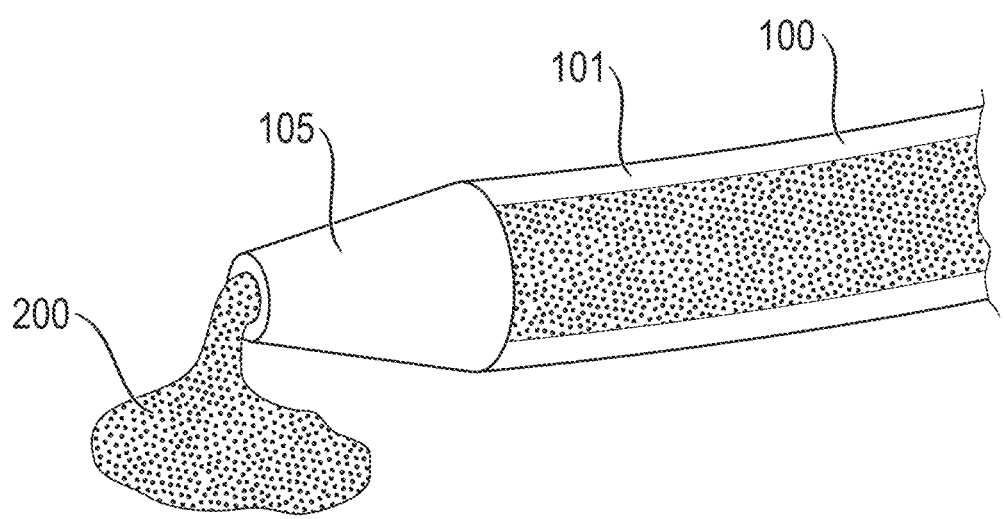
FIG. 2 shows a further schematic illustration of the container for producing a self-curing or dual-curing dental synthetic material composition.

FIG. 2 shows a further schematic illustration of the container 100 for producing a self-curing or dual-curing dental synthetic material composition 200 in accordance with a kneading process. The synthetic material composition 200 is produced by mixing the two synthetic material components 103-1 and 103-2 and can be pressed out of the container 100.

The synthetic material composition 200 forms e.g. a paste for a stoppable dental formulation having a viscosity which is in the range of 50-3000 Pas for flowable synthetic material compositions and preferably between 3000-5000 Pas for stoppable synthetic material compositions. The consistency can be adjusted by supplying energy by increasing the temperature, by means of an ultrasound application, or by diluting with a monomer.

If the synthetic material composition 200 is pressed out of the container 100 in the shape of a tube, e.g. by hand, by means of a plunger or by means of a roller, the synthetic material composition 200 is homogeneously mixed. The synthetic material composition 200 can be self-curing or dual-curing and can be output completely from the container 100.

Figure 3:
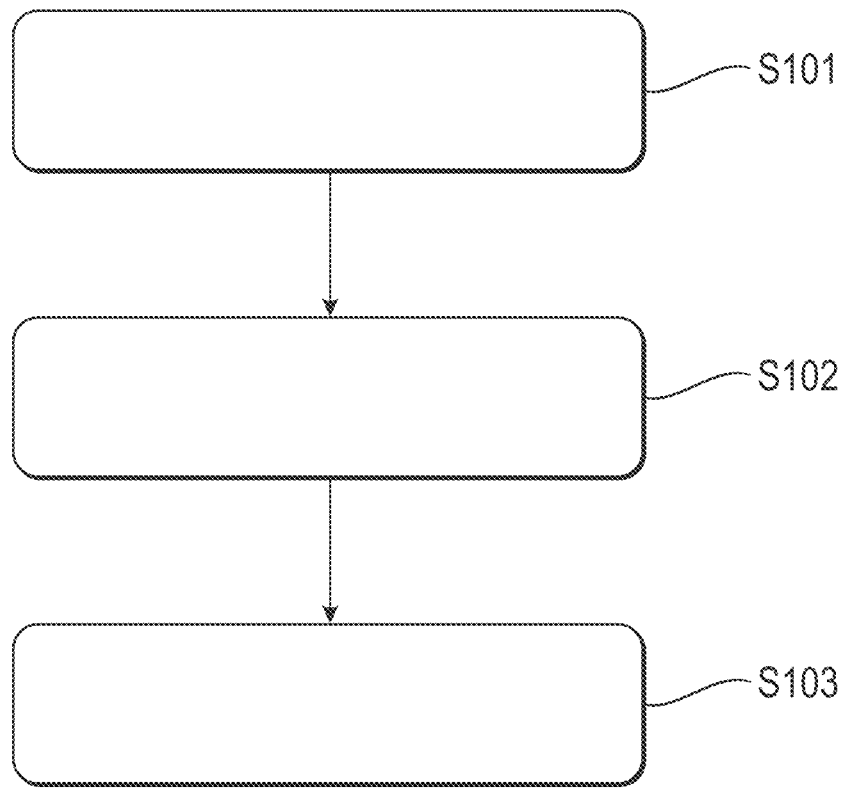
FIG. 3 shows a block diagram of a method for producing a self-curing dental synthetic material composition.

FIG. 3 shows a block diagram of a method for producing a self-curing dental synthetic material composition 200. The two synthetic material components 103-1 and 103-2 are located within the container 100 in an unmixed state, in which the first synthetic material component 103-1 and the second synthetic material component 103-2 are present in different spatial volume regions of the container 100.

In the first step S101, the container 100 can be heated initially to a predetermined temperature. As a result, thorough mixing of the two synthetic material components 103-1 and 103-2 can be accelerated and improved. By heating, mixing durations of a few minutes can be achieved. For example, the closed container 100 in the shape of a tube is heated in a heating cabinet to 80° C. and is then rolled by hand with a certain pressure on a heating plate which is likewise at 80° C.

Part of a mixing unit having a rotor and a stator, or the entire mixing unit, can also be heated in order to heat the material. Metering of the material, mixing and heating can take place in a device without manual intermediate steps. Examples of heating temperatures depend on the materials being used, and may include but are not limited to temperatures no higher than 500° C. are used, preferably up to 275° C., more preferably from about 30° to 60° C., or 35° to 50° C.

Then, in step S102 the container 100 with the deformable wall 101 is mechanically kneaded in order to achieve a homogeneous mixture of the two synthetic material components 103-1 and 103-2 within the container 100. Kneading includes, but is not limited to, milling, rolling, shaping or compressing the container 100.

In step S103, the synthetic material composition 200 thus produced from the two synthetic material components 103-1 and 103-2 is pressed out of the container 100 in order for it to be able to be processed according to its purpose, such as e.g. as a dental filling or as a glue. By mixing the synthetic material components 103-1 and 103-2, the synthetic material composition 200 is cured. The method provides the technical advantage that even small amounts of the synthetic material composition 200 can be simply and rapidly produced with a precise mixing ratio for dental application.

All features explained and illustrated in conjunction with individual embodiments of the invention can be provided in different combinations in the subject matter in accordance with the invention in order to achieve the advantageous effects thereof at the same time.

All the method steps can be implemented by devices which are suitable for carrying out the respective method step. All functions which are carried out by features relating to the container can be a method step of a method.

The scope of protection of the present invention is set by the claims and is not limited by the features explained in the description or shown in the figures.

LIST OF REFERENCE SIGNS

100 Container
101 Wall
103-1 Synthetic material component
103-2 Synthetic material component
105 Spout
200 Synthetic material composition

The invention claimed is:

1. A container (100) for producing a self-curing or dual-curing dental synthetic material composition (200) comprising
    a deformable wall (101),
    a first synthetic material component (103-1); and
    a second synthetic material component (103-2) for curing the synthetic material composition (200) or starting a curing reaction,
    wherein the synthetic material composition (200) comprising the mixed first synthetic material component (103-1) and second synthetic material component (103-2) has a viscosity which is in the range of 50-3000 Pas for flowable synthetic material compositions and between 3000-50000 Pas for stoppable synthetic material compositions.

2. The container (100) as claimed in claim 1, wherein the container (100) is in the shape of a tube or bag.

3. The container (100) as claimed in claim 1, wherein the deformable wall (101) is formed from silicone.

4. The container (100) as claimed in claim 1, wherein the deformable wall (101) is transparent in a wavelength range of 390 nm to 520 nm.

5. The container (100) as claimed in claim 1, wherein the first synthetic material component (103-1) and/or the second synthetic material component (103-2) are arranged in the form of a string within the container (100).

6. The container (100) as claimed in claim 5, wherein the first synthetic material component (103-1) in the form of a string and the second synthetic material component (103-2) in the form of a string are twisted.

7. The container (100) as claimed in claim 1, wherein the first synthetic material component (103-1) comprises a polymerizable organic matrix having a mixture of monomers, initiator components, stabilisers and pigments.

8. The container (100) as claimed in claim 1, wherein the first and/or second synthetic material components (103-1, 103-2) are in the form of a powder, paste, liquid or gel.

9. The container (100) as claimed in claim 1, wherein the container (100) comprises a spout (105) for squeezing out the synthetic material composition (200).

10. A method for producing a self-curing or dual-curing dental synthetic material composition (200), comprising:
    kneading (S101) a container (100) having a deformable wall (101) and comprising a first synthetic material component (103-1) and a second synthetic material component (103-2) for curing the synthetic material composition (200) or starting a curing reaction, wherein the synthetic material composition (200) comprising the mixed first synthetic material component (103-1) and second synthetic material component (103-2) has a viscosity which is in the range of 50-3000 Pas for flowable synthetic material compositions and between 3000-50000 Pas for stoppable synthetic material compositions.

11. The method as claimed in claim 10,
wherein the container (100) is heated to a predetermined temperature before or during the step (S101) of kneading.

12. The method as claimed in claim 10,
wherein the kneading or mixing of the first and second synthetic material components (103-1, 103-2) is performed at low pressure or under vacuum.

* * * * *